United States Patent [19]

Izod et al.

[11] 4,375,568

[45] Mar. 1, 1983

[54] CHROMATOGRAPHIC SEPARATIONS USING A UNIQUE SILICA POLYMORPH

[75] Inventors: Thomas P. J. Izod, Holliston, Mass.; Jack A. Duisman, El Cerrito, Calif.

[73] Assignee: Union Carbide Corporation, Danbury, Conn.

[21] Appl. No.: 231,406

[22] Filed: Feb. 4, 1981

[51] Int. Cl.³ .................... C07C 37/82; C07C 29/76
[52] U.S. Cl. .................................. 568/758; 568/917
[58] Field of Search ............... 568/758, 917, 913, 749, 568/750

[56] References Cited

U.S. PATENT DOCUMENTS

| | | | |
|---|---|---|---|
| 3,557,531 | 1/1971 | McKinney | 55/67 |
| 3,626,666 | 12/1971 | Drinkard | 55/67 |
| 3,699,182 | 10/1972 | Cattanach | 260/674 SA |
| 3,719,026 | 3/1973 | Sand | 55/33 |
| 3,732,326 | 5/1973 | Chen | 260/676 MS |
| 3,835,043 | 9/1974 | Geissler et al. | 210/316 |
| 4,073,865 | 2/1978 | Flanigen et al. | 423/339 |

OTHER PUBLICATIONS

Flanigen et al., Silicalite, A New Hydrophobic Crystalline Silica Molecular Sieve, Nature vol. 271; pp. 512-516, Feb. 9, 1978.

*Primary Examiner*—Werren B. Lone
*Attorney, Agent, or Firm*—Gary L. Wamer

[57] ABSTRACT

Chromatographic separation of mixtures containing low molecular weight alcohols, ethylene glycol, phenol and water are made in the liquid and gas phase using as a column packing a unique crystalline silica polymorph, synthesized hydrothermally from a reaction system containing silica, water, an alkylonium base and fluoride anions.

8 Claims, 11 Drawing Figures

CHROMATOGRAPHIC SEPARATIONS USING A UNIQUE SILICA POLYMORPH

BACKGROUND OF THE INVENTION

1. Field of the Invention

The invention relates to the chromatographic separation of mixtures containing certain low molecular weight alcohols, ethylene glycol, phenol and water. This is accomplished by the use of a unique crystalline polymorph, hereinafter called "F-silicalite," as the fixed-bed or column packing. The properties of F-silicalite allow a sharp separation between components of a sample mixture, providing for good resolution of peaks on a chromatogram and quantitative analysis of the mixture.

Chromatography is a process whereby different types of molecules are separated one from another. A sample mixture is introduced into a fluid phase or carrier stream which is then passed over a stationary phase or fixed bed. The fixed bed is of a composition that interacts with the components of the sample mixture in the carrier stream. Generally the fixed bed interacts differently or selectively with the individual components so that the components migrate at different rates through the fixed bed, thus achieving a separation.

The carrier stream may be a gas or a liquid, in which case the method is termed either gas chromatography or liquid chromatography, respectively. In gas chromatography the gas phase may be contacted with a liquid surface. In this method, termed gas-liquid chromatography, the liquid surface may be in the form of a liquid on the surface of a solid support. In the operation of a typical chromatographic apparatus, the mixture to be analyzed is momentarily or intermittently injected into a carrier stream which is then passed through the fixed bed. Due to the separative properties of the composition of the fixed bed, components of the mixture are separated so that the relative concentrations of components of the mixture in the carrier stream vary with time as it emerges from the fixed bed. This variation in composition can be detected by measurement of an appropriate physical property, such as the index of refraction or the thermal conductivity. When the apparatus is provided with a recording means, such as a chart recorder, the variation is manifested in the form of peaks on a chart called a chromatogram, with each peak corresponding to a component in the mixture. FIGS. 1, 2, 4, 6–8, 10 and 11 show examples of such chromatograms. The retention time or the position of the maximum of a peak on the chromatogram is dependent on the migration time of the corresponding component through the fixed bed. Thus, by choosing a composition for the fixed bed of known properties and setting appropriate operating conditions, a person skilled in the art can identify components of a mixture by the positions of the peaks or retention times on the chromatogram.

It is, therefore, desirable that the fixed bed have properties that allow for selective separation of components in a mixture in a manner that results in sharp, well-defined peaks. A composition may exhibit separative properties for a mixture but will be unsuitable for chromatographic applications if it separate components into broad, unresolvable peaks. By measuring areas under the peaks, for example by using an integrator, it is often possible to determine the relative concentrations of a component in various mixtures. If the peaks are too broad or overlap such that areas under individual peaks cannot be resolved this may not only lead to difficulty in identifying the components but also make it impossible to determine the relative concentrations.

It is therefore desirable that the separative properties of the composition of the fixed bed be such that good separation and resolution of the peaks on a chromatogram be possible.

Mixtures of compounds with similar properties are often difficult to separate under chromatographic conditions. These include, among others, isotopic mixtures and mixtures of chemically-related compounds such as organic compounds with the same functional group.

One such class of mixtures are those polar compounds containing the —O—H or hydroxyl functional group. Included in this class are mixtures of alcohols, water and other compounds such as glycols and phenols.

It is an object of the invention to provide a process for the separation of mixtures of this type. Specifically, an object of the invention is to provide for the separation of mixtures containing methanol, ethanol, 1-propanol, 2-propanol, ethylene glycol, phenol and water.

2. Prior Art

As indicated above, the composition of the fixed bed must act selectively on the components of a mixture to effect a separation. One class of compounds that has been suggested for use as a fixed bed is zeolites. Zeolites are crystalline aluminosilicates having the general formula in terms of moles of oxides;

$$xM_{2/n}O:Al_2O_3:ySiO_2:zH_2O,$$

where M is an exchangeable cation, n is the valence of M and x, y and z are molar ratios of the corresponding oxide to $Al_2O_3$.

Zeolites act as molecular sieves. They can, therefore, be used for separations based on molecular size of a component molecule. The use of zeolites in chromatography, based on this property, is disclosed in U.S. Pat. No. 3,626,666 to B. M. Drinkard and U.S. Pat. No. 3,699,182 to J. Cattanach. In these references, zeolites ZSM-5, ZSM-8 and calcium zeolite 5A are used for separations of mixtures such as aromatic isomers, biphenyls and benzene with polysubstituted aromatic hydrocarbons.

Some zeolites, principally those with a high silica-to-alumina ratio, exhibit hydrophobic/organophilic properties. These zeolites act selectively on the basis of polarity. An example of such an application is disclosed in U.S. Pat. No. 3,732,326 to N. Y. Chen wherein certain polar-selective zeolites having a high silica-to-alumina ratio, such as zeolite ZSM-5, are used in the separation of mixtures such as cyclohexane with methanol and benzene with butanol, using chromatographic techniques.

SUMMARY OF THE INVENTION

The objects of the invention are accomplished by the use of a unique silica polymorph as the fixed bed. This silica polymorph, denoted F-silicalite, is synthesized hydrothermally from a reaction system containing silica, water, an alkylonium base and fluoride anions. The composition and a process of manufacture are disclosed in U.S. Pat. No. 4,073,865 to E. M. Flanigen and R. L. Patton.

To demonstrate the properties of F-silicalite as compared to similar compositions, tests were made under similar conditions using a zeolite, silicalite and F-silicalite as the fixed bed in a chromatographic apparatus. The zeolite used was one with a high silica-to-alumina ratio having properties similar to ZSM-5 where potassium is the exchangeable cation. The composition and a method of manufacture of ZSM-5 are disclosed in U.S. Pat. No. 3,702,886 to R. J. Argauer and G. R. Landolt.

Silicalite, disclosed in U.S. Pat. No. 4,061,724 to R. W. Grose and E. M. Flanigen, is a crystalline silica polymorph with a crystal structure similar to a zeolite. Unlike a zeolite it does not contain structure alumina and therefore does not exhibit ion-exchange properties. It is hydrophobic and is suitable for separating organic materials from water.

F-silicalite is a silica polymorph with properties quite similar to silicalite. It is distinguishable from silicalite by its X-ray diffraction pattern, water adsorption properties and infrared absorption spectrum. It also exhibits an exceptional degree of hydrophobicity.

Using a solution of methanol, ethanol, 1-propanol and 2-propanol in water, tests were run using the above-referenced zeolite as the fixed bed in a liquid chromatographic apparatus. Water was used as a carrier fluid. The peaks of the chromatograph (FIG. 11) showed considerable broadening such that it was only possible to measure the peak corresponding to methanol meaningfully.

Liquid chromatography tests using water as a carrier fluid were run using silicalite with a sample solution of methanol, ethanol, 1-propanol, 2-propanol and water. The peaks on the chromatogram showed broadening such that only peaks corresponding to methanol and ethanol were recorded.

Although zeolites of the ZSM-5 family and also silicalite exhibit hydrophobic properties, they did not exhibit suitable separatory properties for chromatographic separations of the above-mentioned alcohols.

However, F-silicalite surprisingly proved to be a suitable composition for the chromatographic separation of alcohols.

Use of F-silicalite to separate a solution of methanol, ethanol, 1-propanol and 2-propanol in water in tests like those above produced a chromatogram with separate and distinct peaks corresponding to the solution components. Heretofore there has not been in the art a suitable composition for separating solutions of the above mentioned low molecular weight alcohols in liquid chromatography. Use of F-silicalite, therefore, represents a major advantage over the prior art. It has been found to be equally useful in gas and liquid chromatography. F-silicalite also has been found suitable in chromatographic separation of solutions containing ethylene glycol and phenol, both of which are chemically related to alcohols.

In accordance with the invention a process is provided for the chromatographic separation of mixtures of compounds having a hydroxyl functional group, said mixtures containing (a) two or more members of the group consisting of ethylene glycol, methanol, ethanol, 2-propanol, 1-propanol and water or (b) phenol and water, which comprises passing said mixtures over a fixed bed of silicalite.

The invention can alternately be described as providing a method of chromatographically separating fluid sample mixtures of the above composition, which comprises intermittently injecting a fluid sample mixture into a carrier fluid and passing said carrier fluid through a chromatographic separation column containing a fixed bed of F-silicalite.

DETAILED DESCRIPTION OF THE INVENTION

As indicated above, the process of the invention involves the use of F-silicalite in liquid and gas chromatography. F-silicalite for use in the process of the invention can be prepared by the process which comprises providing a reaction mixture having a pH below 11, preferably within the range of 7 to 11, more preferably 7.4 to 10, which in terms of moles of oxides contains from 150 to 1500 moles $H_2O$, from 13 to 50 moles $SiO_2$, from 2 to 12 moles of fluoride ion and from 0 to 20 moles, preferably 0 to 6 moles, $M_2O$ wherein M represents an alkali metal cation, each of the aforesaid reagents being present per mole of $Q_2O$ wherein Q represents a quaternary cation having the formula $(R_4X)+$, in which each R represents hydrogen or an alkyl group containing from 2 to 6 carbon atoms, and X represents phosphorous or nitrogen, heating the reaction mixture thus provided at a temperature of from 100° to 250° C. until a crystalline hydrated precursor is formed, usually about 50 to 150 hours, isolating said crystalline precursor and calcining same at a temperature of from 400° C. to 1000° C.

Further details of the synthesis of F-silicalite are found in the above cited U.S. Pat. No. 4,073,865 to E. M. Flanigen and R. L. Patton, which patent is incorporated into this specification by reference.

In general a small crystal size of F-silicalite will result in less broadening of the peaks. However, too small a crystal size will cause an excessive pressure drop over the length of the fixed bed. In the examples below the crystal size was in the range of 20×20×150 microns. At this size the chromagraphic apparatus can be operated under low pressures at fairly high carrier flow rates. However any crystal size allowing normal operating conditions is suitable in the invention.

It is preferred that the F-silicalite be as free from impurity as is possible. It is, therefore, recommended that it be acid-washed and calcined at about 600° C. for at least two hours.

The following examples illustrate the preferred embodiments of the invention. Shown are examples of liquid chromatography and gas chromatography. In all the examples the F-silicalite used was acid-washed and calcined at 600° C. for 2 hours. The crystal size was about 20×20×150 microns. In both the liquid and gas applications the pressure drop across the bed was near zero pounds per square inch.

Examples 1-12 illustrate the process of the invention in liquid chromatography. In these examples, a liquid chromatograph apparatus typical in the art was used. The apparatus was a "Chromatronix 3500" liquid chromatograph with an L.D.C., Model 1107 refractometer as a detector (from Chromatronix, Inc.), peak retention times and peak areas were obtained with a Model 3373B integrator from Hewlett-Packard Retention time is defined as the time from sample injection to the occurrence of the maximum of the peak. The sample volume for each example was 1.0 microliter (ul.). The carrier fluid was water. In Examples 1 to 5 the column containing the fixed bed was 23 cm long and had an internal diameter of 1.5 mm. The weight of the F-silicalite used in the fixed bed was 0.54 grams. In Examples 6–12 a column 47 cm long, having an inside diameter of 4.5 mm and containing 3.80 grams of of F-silicalite was used.

EXAMPLE 1

Figure 1:
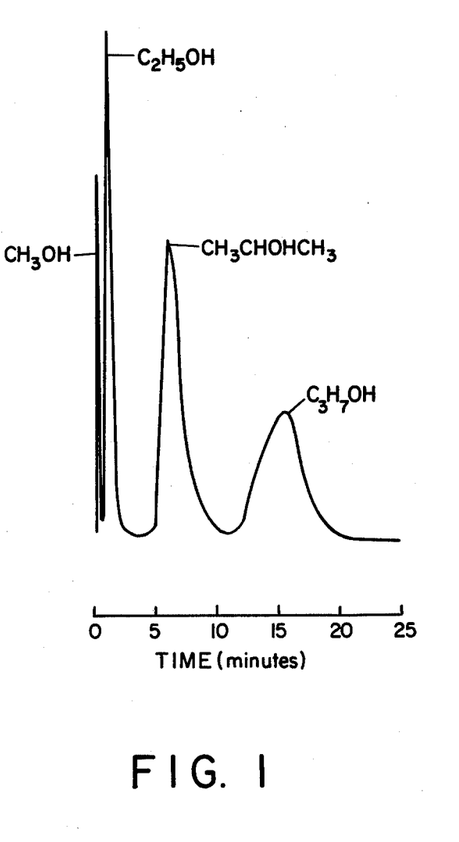
FIGS. 1, 2, 4, 6-8, 10 and 11 are chromatograms used to illustrate the invention. In these chromatograms the abscissa represents time in minutes and the ordinate represents peak height.

A sample solution composed of 1% methanol, 1% ethanol, 1% 1-propanol and 1% 2-propanol in water was tested. The carrier flow rate was set at 2.0 ml/min. FIG. 1 shows the chromatogram for this example.

EXAMPLE 2

Figure 2:
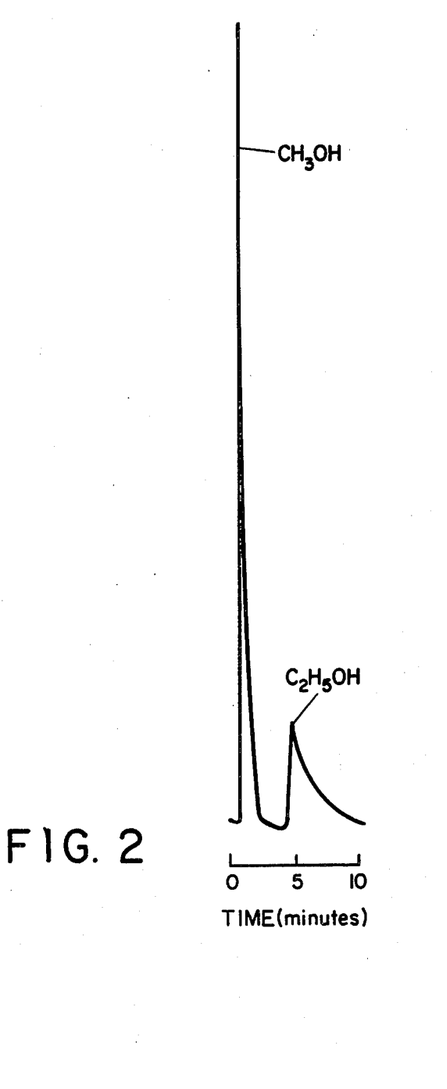

A sample solution composed of 2% methanol and 0.5% ethanol in water was tested. The carrier flow rate was set at 0.8 ml/min. FIG. 2 shows the chromatogram for this example.

FIGS. 1 and 2 show the peaks corresponding to the alcohol components to be distinct and sharp for each example. This good separation allows for quantitative analysis of alcohol solutions as illustrated by Examples 3 to 5 below.

EXAMPLES 3 TO 5

Solutions of methanol, ethanol and 2-propanol were tested. The carrier flow rate was 2.0 ml/min for these examples. A summary of the results is shown in Table A. The peak areas are in arbitrary units related to the operating conditions of the chromatograph and chart recorder.

TABLE A

| Component | Vol. - % | Retention Time (min) | Peak Area (units) |
| --- | --- | --- | --- |
| Example 3: | | | |
| Methanol | 2.0 | 0.89 | 750.3 |
| Ethanol | 2.0 | 1.99 | 2308. |
| 2-Propanol | 2.0 | 7.54 | 3017. |
| Example 4: | | | |
| Methanol | 1.0 | 0.86 | 375.1 |
| Ethanol | 1.0 | 1.93 | 1162. |
| 2-Propanol | 1.0 | 7.82 | 1473. |
| Example 5: | | | |
| Methanol | 0.5 | 0.85 | 180.6 |
| Ethanol | 0.5 | 1.93 | 550.2 |
| 2-Propanol | 0.5 | 8.31 | 675.0 |

Figure 3:
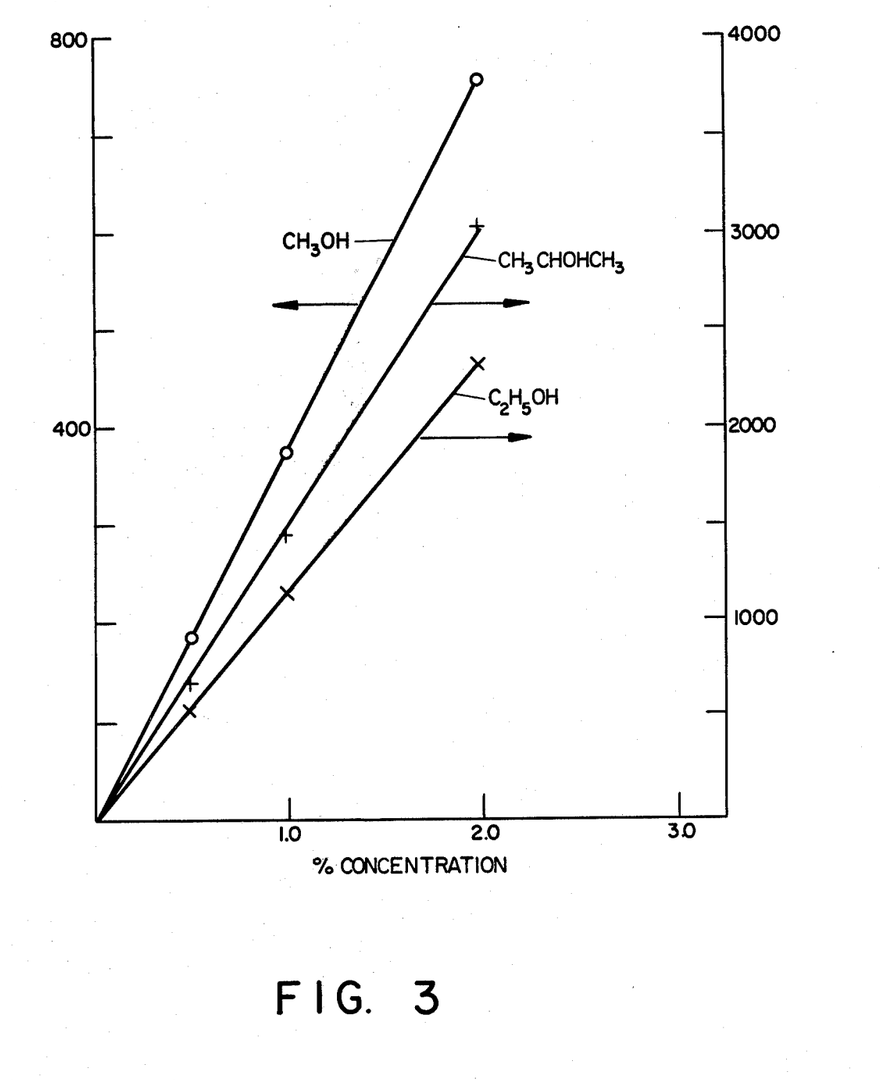
FIGS. 3, 5 and 9 are graphs used to demonstrate the invention.

FIG. 3 shows a plot of the component concentrations versus the peak area for each alcohol component. As shown in FIG. 3 the peak areas are linear in relation to the concentrations. This is very significant in that it allows quantitative analysis of solutions. Using a standard solution of known concentration in volume-percent, one can compute concentration of a component by the following relation; (concentration of sample)=- (concentration of standard)×(peak area of sample/peak area of standard). The concentration of the standard should be within the general range of that of the sample. The linear relationship may not be valid for all concentrations outside of the range of the above examples, so tests of standard solutions within a desired range should be made to ensure the relationship is still linear.

EXAMPLE 6

Figure 4:
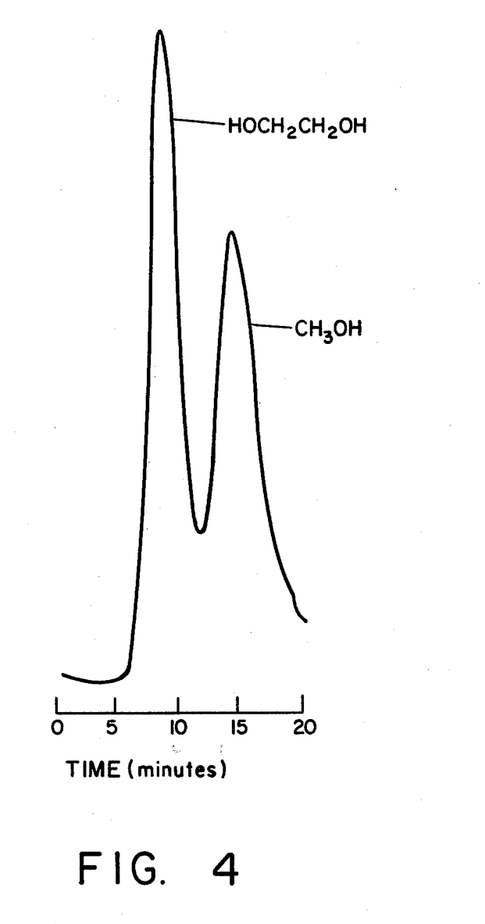

A sample solution containing ethylene glycol and methanol was tested. The carrier flow rate was set at 0.8 ml/min. As shown in FIG. 4 the retention times for methanol and ethylene glycol are similar. However, the peaks are sufficiently separate for useful analysis. As shown in FIG. 4, the retention time of ethylene glycol is less than methanol. Therefore, for solutions containing ethylene glycol, methanol, ethanol, 2-propanol, and 1-propanol, the component peaks on the chromatogram will emerge in the above indicated order.

EXAMPLES 7-12

Solutions of ethylene glycol in water over a range of concentrations were tested. The carrier flow rate was 3.2 ml/min. for these examples. Table B shows a summary of these tests.

TABLE B

| Example No. | Concentration (% by volume) | Peak Area (units) |
| --- | --- | --- |
| 7 | 10 | 1610 |
| 8 | 8 | 1295 |
| 9 | 6 | 960.3 |
| 10 | 4 | 642.5 |
| 11 | 2 | 321.2 |
| 12 | 1 | 158.6 |

Figure 5:
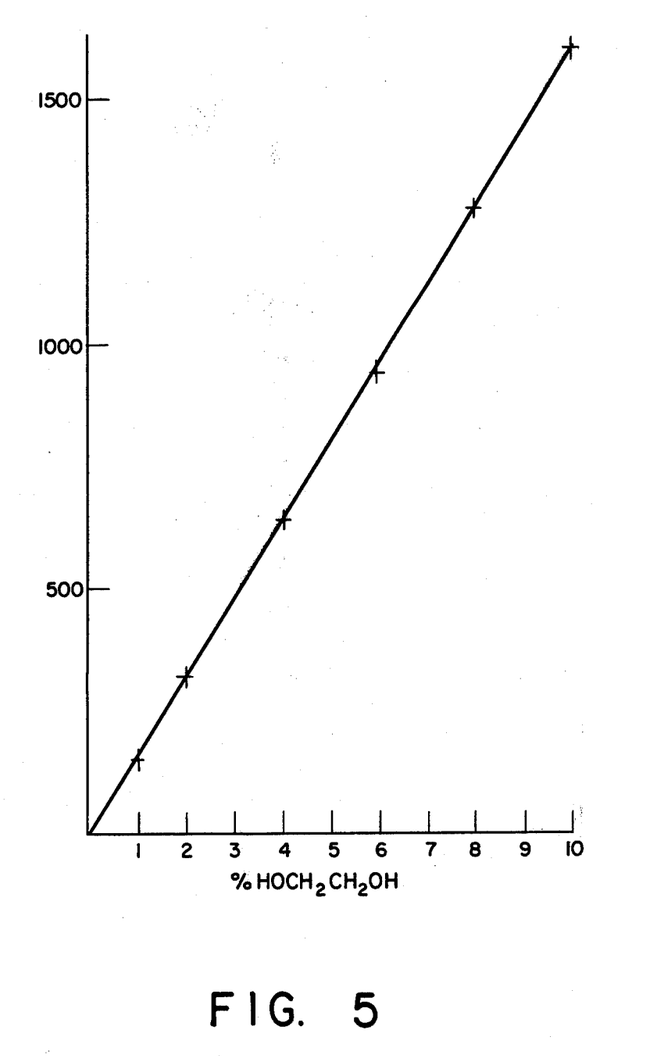

FIG. 5 is a plot showing a linear relationship between component peak area and concentration. In the same manner as explained above, this allows for quantitative analysis of ethylene glycol solutions.

Examples 13 to 19 demonstrate embodiments of the invention using gas chromatography. A column 6 feet long and ¼" in diameter was packed with approximately 15 grams of F-silicalite, incorporated into a gas chromatograph and baked for 2 hours at 300° C. with a helium purge. The gas chromatograph was a "Varian" 1800 G.C. equipped with a thermal conductivity detector (from Varion Associates). Helium gas was used as a carrier.

EXAMPLE 13

Figure 6:
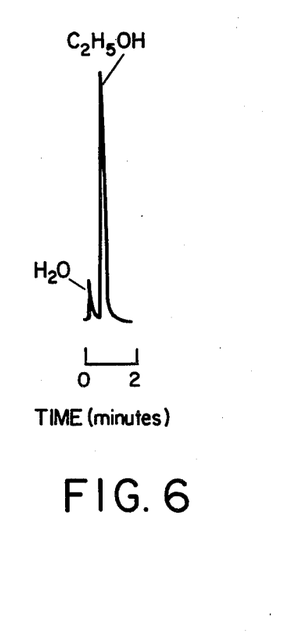
Figure 7:
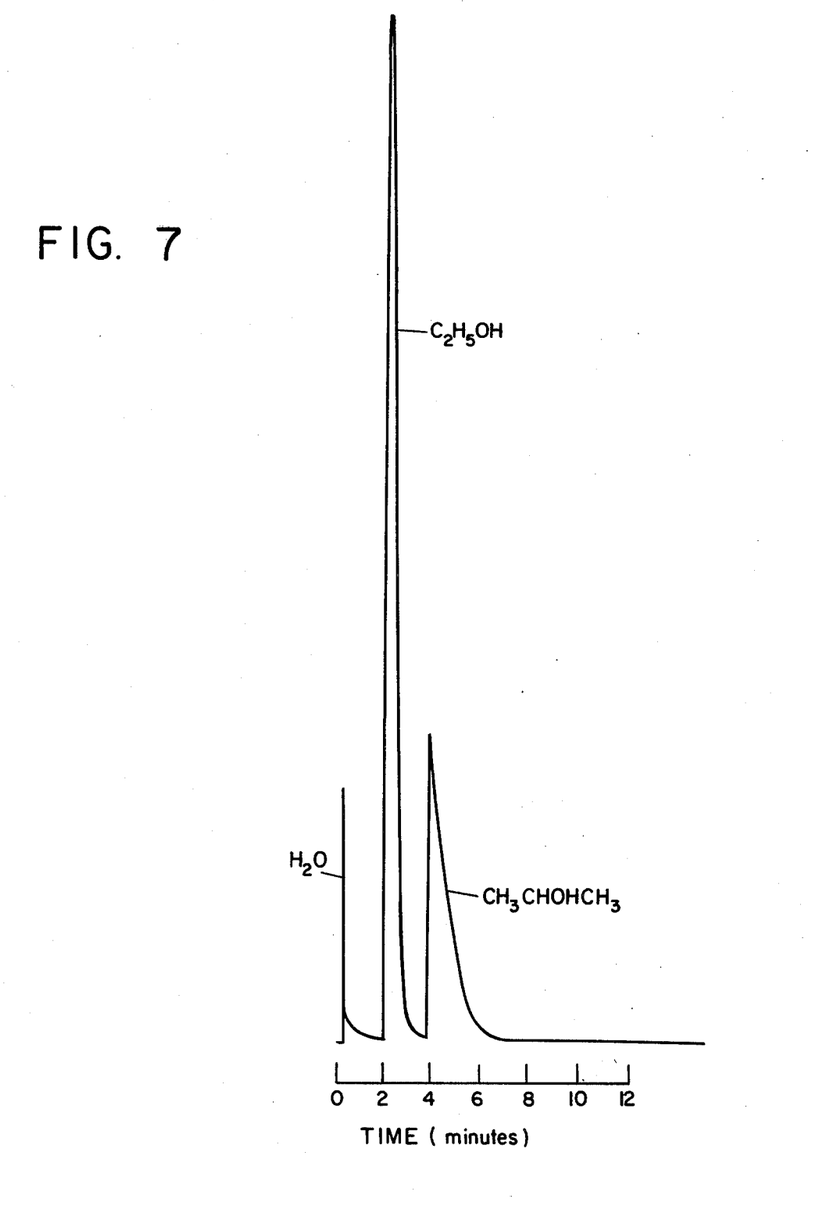

A solutin of 95% ethanol and 5% water was tested. The helium flow rate was 75 ml/min. The column temperature was 190° C. and the detector temperature was 250° C. The sample volumes were 5 µl. In the chromatogram labeled FIG. 6 is shown a good separation of the ethanol and water peaks.

EXAMPLE 14

A solution consisting of 2-propanol, ethanol and water was tested. The helium flow was 75 ml/min. The column temperature was 190° C. and the detector temperature was 250° C. The sample volume was 5 µl. As shown in the chromatogram in FIG. 7, the component peaks are distinct and well separated.

EXAMPLES 15-18

Samples of a commercial-grade ethylene glycol containing a trace of water were tested. The helium flow rate was 75 ml/min, the column temperature was 200° C. and the detector temperature was 250° C. The sample volumes are shown below in Table C.

TABLE C

| Example No. | Sample Volume, µl |
| --- | --- |
| 15 | 5.0 |
| 16 | 3.0 |
| 17 | 2.0 |
| 18 | 0.5 |

Figure 8:
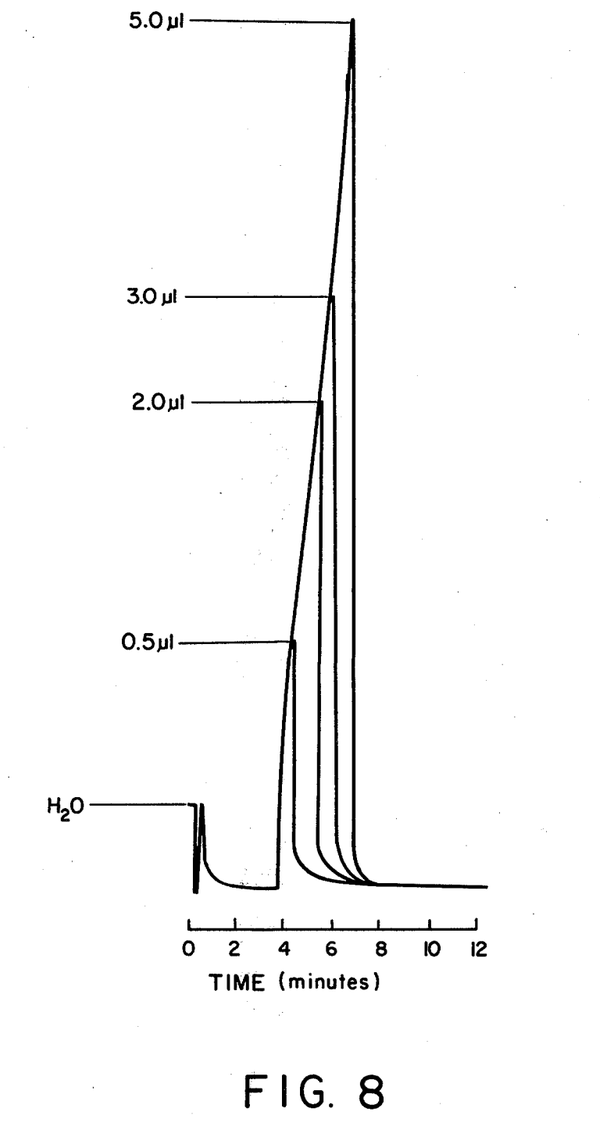
Figure 9:
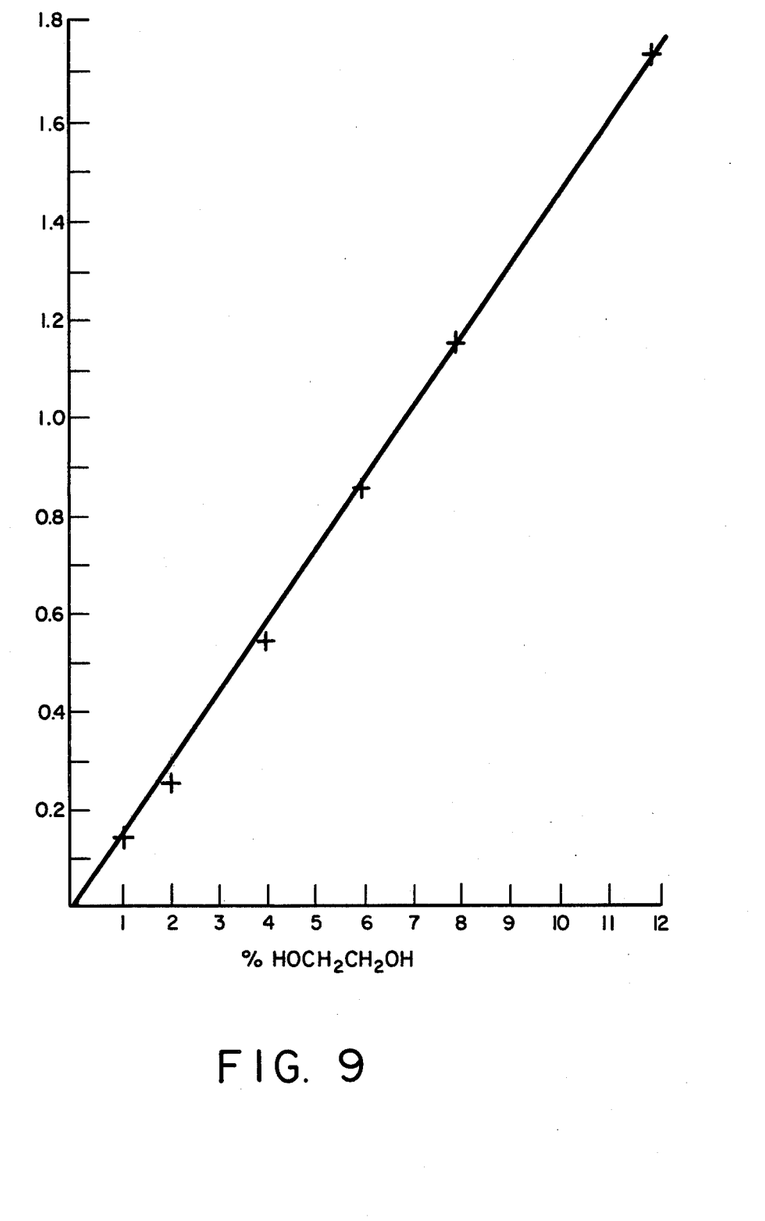

FIG. 8 shows the resulting chromatograms superimposed. The ethylene glycol concentrations (by volume)

in the carrier gas and the corresponding peak area were plotted in FIG. 9. Here is demonstrated the feasibility of quantitative analysis of ethylenee glycol solutions using gas chromatography in the same manner explained above for liquid chromatography.

The small peak on the left of FIG. 8 corresponds to the trace of water (about 0.1%) present in the commercial ethylene glycol tested. These examples and also Examples 13 and 14 show how the process of the invention can be used to detect small amounts of water in solutions of alcohols and ethylene glycol.

EXAMPLE 19

Figure 10:
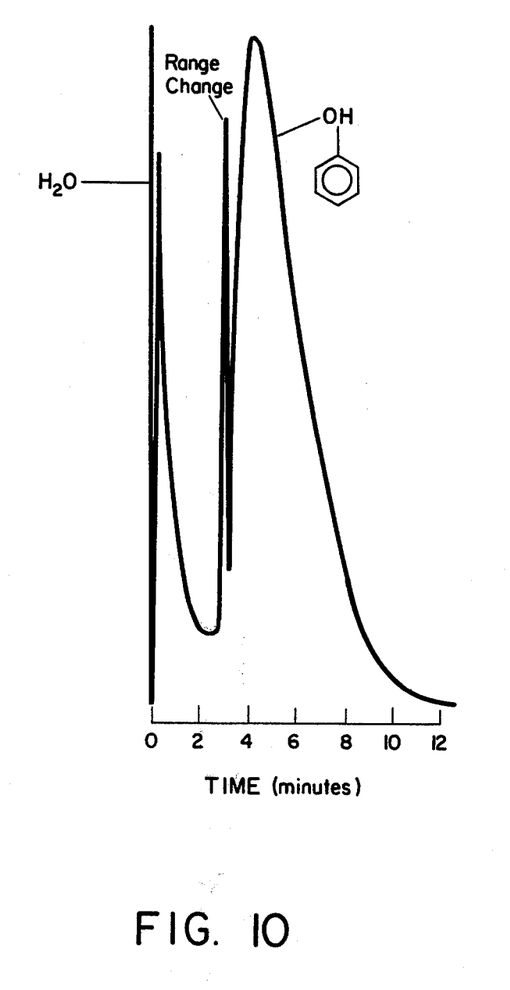
Figure 11:
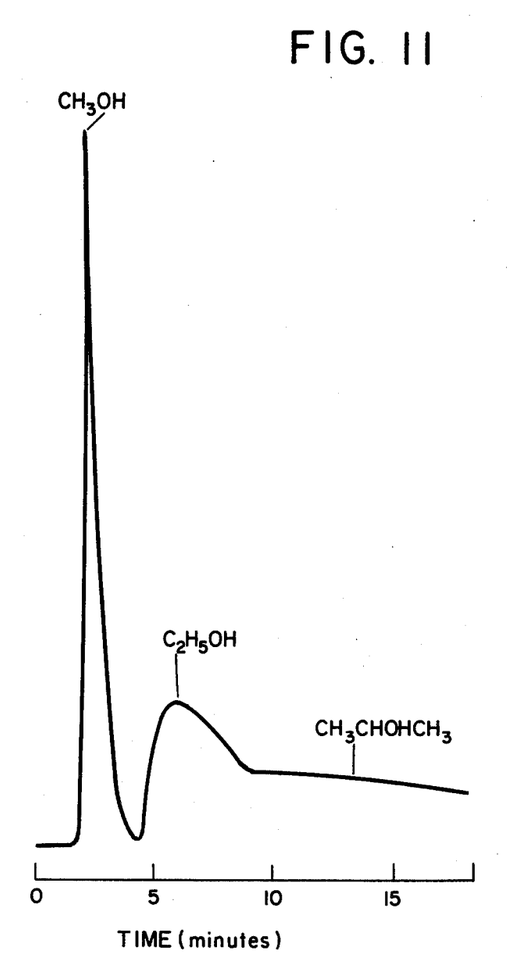

This example demonstrates the chromatographic separation of phenol and water. The gas-chromatograph of Examples 13 to 18 was used except the column for the fixed bed was 47 cm long, had a diameter of 4.5 mm and contained 3.80 grams of F-silicalite. The helium flow was 75 ml/min. the column temperature was 250° C. and the sample size was 5.0 μl. A reagent-grade phenol containing a trace of water was tested; FIG. 10 shows a distinct and separated peak corresponding to the water. This shows the usefulness of the process of the invention in detecting water in phenol.

What is claimed is:

1. A process for the chromatograpic separation of mixtures of compounds having a hydroxyl functional group, said mixtures containing,
    (a) two or more members of the group consisting of ethylene glycol, methanol, ethanol, 2-propanol, 1-propanol and water or
    (b) phenol and water, which comprises passing said mixtures over a fixed bed of F-silicalite.

2. The process of claim 1 wherein the mixture is in the liquid phase and contains two or more members of the group consisting of methanol, ethanol, 2-propanol, 1-propanol and water.

3. The process of claim 1 wherein the mixture is in the gas phase and contains two or more members of the group consisting of ethanol, 2-propanol and water.

4. The process of claim 1 wherein the mixture is in the liquid phase and contains ethylene glycol and water.

5. The process of claim 1 wherein the mixture is in the gas phase and contains ethylene glycol and water.

6. The process of claim 1 wherein the mixture is in the gas phase and contains phenol and water.

7. A method of chromatographically separating a fluid sample mixture which comprises intermittently injecting said fluid sample mixture into a carrier fluid and passing said carrier fluid through a chromatographic separating column containing a fixed bed of F-silicalite; said sample fluid mixture containing two or more members of the group consisting of ethylene glycol, methanol, ethanol, 2-propanol, 1-propanol and water.

8. A method of chromatographically separating a fluid sample mixture which comprises intermittently injecting said fluid sample mixture into a carrier fluid and passing said carrier fluid through a chromatographic separation column containing a fixed bed of F-silicalite; said sample fluid mixture containing phenol and water.

* * * * *